(12) United States Patent
Cope et al.

(10) Patent No.: US 8,727,250 B2
(45) Date of Patent: May 20, 2014

(54) SYSTEM AND METHOD FOR CREATING A TEST SAMPLE FROM INDIVIDUAL SEEDS OR TISSUE STRUCTURES

(71) Applicant: Pioneer Hi-Bred International, Inc., Johnston, IA (US)

(72) Inventors: Jason M. Cope, Ankeny, IA (US); David Kurth, Grimes, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/957,580

(22) Filed: Aug. 2, 2013

(65) Prior Publication Data

US 2013/0313347 A1 Nov. 28, 2013

Related U.S. Application Data

(62) Division of application No. 12/880,489, filed on Sep. 13, 2010, now Pat. No. 8,523,092.

(60) Provisional application No. 61/242,181, filed on Sep. 14, 2009.

(51) Int. Cl.
*B02C 17/20* (2006.01)
*B02C 19/00* (2006.01)

(52) U.S. Cl.
USPC ........................................... 241/68; 241/184

(58) Field of Classification Search
USPC .................................. 241/6, 30, 68, 170–184
See application file for complete search history.

(56) References Cited

U.S. PATENT DOCUMENTS

| | | | | |
|---|---|---|---|---|
| 4,712,333 | A * | 12/1987 | Lofton ........................... | 451/330 |
| 5,183,214 | A * | 2/1993 | Zakheim et al. ................. | 241/30 |
| 6,880,771 | B2 * | 4/2005 | Deppermann ..................... | 241/2 |
| 7,608,755 | B2 * | 10/2009 | Shi et al. ......................... | 800/285 |
| 8,348,183 | B2 * | 1/2013 | Mertens et al. ................... | 241/2 |
| 2003/0079247 | A1 * | 4/2003 | Shi et al. ......................... | 800/278 |
| 2008/0203201 | A1 * | 8/2008 | Deppermann et al. .......... | 241/25 |

* cited by examiner

*Primary Examiner* — Mark Rosenbaum
(74) *Attorney, Agent, or Firm* — Pioneer Hi-Bred Int'l Inc.

(57) ABSTRACT

The present invention is generally directed to a system and method for obtaining a test sample from a seed or seeds. The method generally includes placing at least one seed into a seed sampling chamber, breaking the seed into a plurality of seed particles inside the seed sampling chamber, placing a sampling element into the seed sampling chamber, and collecting at least a portion of the plurality of seed particles with the sampling element by attracting at least a portion of the seed particles to a surface of the sampling element or by forcing at least a portion of the seed particles into a feature of the sampling element. In some embodiments, the method further includes using a sampling element transfer device to transfer the sampling element to an extraction well, which may be used to extract DNA or proteins from the collected portion of seed particles.

17 Claims, 11 Drawing Sheets

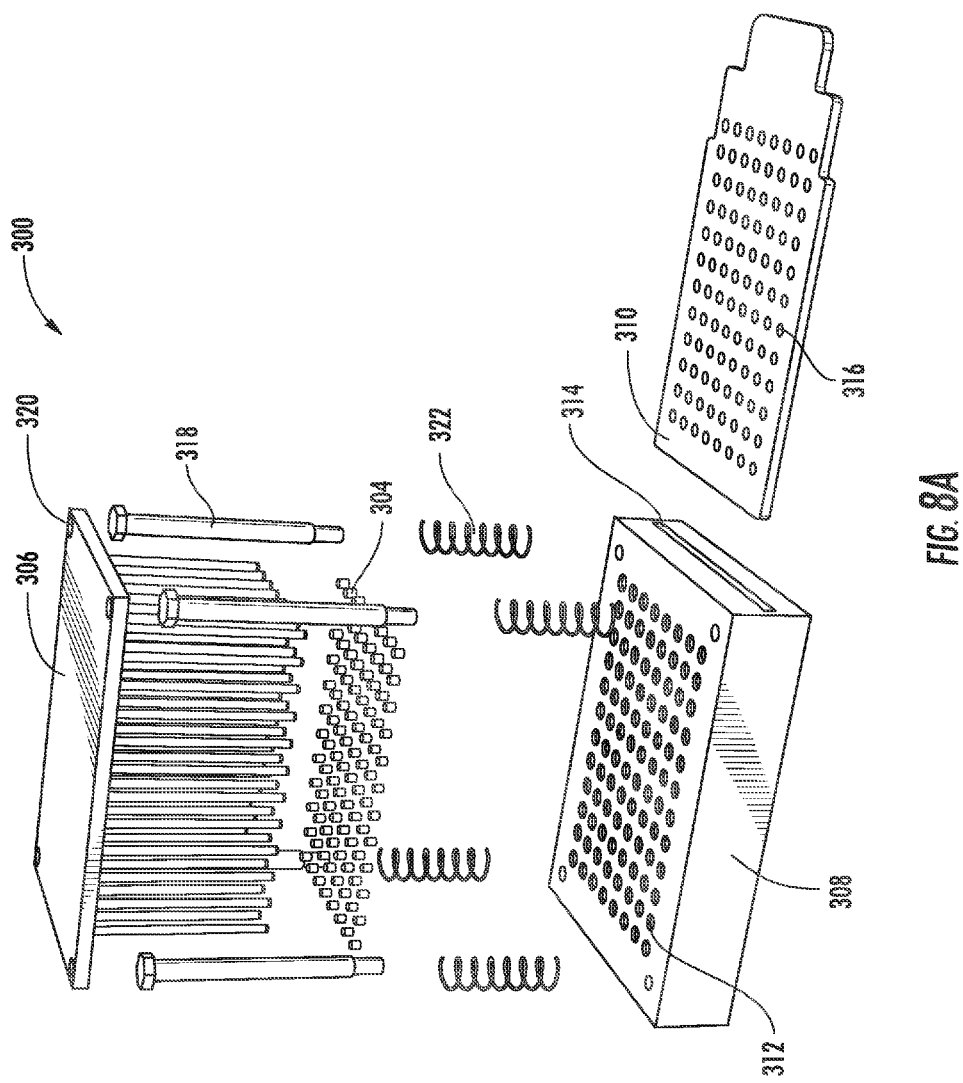

SYSTEM AND METHOD FOR CREATING A TEST SAMPLE FROM INDIVIDUAL SEEDS OR TISSUE STRUCTURES

CROSS-REFERENCE TO RELATED APPLICATIONS

The present application is a divisional application of U.S. patent application Ser. No. 12/880,489, filed Sep. 13, 2010, which claims priority from U.S. Provisional Application No. 61/242,181, filed Sep. 14, 2009, each of which is hereby incorporated herein by reference in its entirety.

FIELD OF THE INVENTION

The present invention relates generally to systems and methods for obtaining samples of seeds. More specifically, the present invention provides a system and method for obtaining tissue samples from one or more individual seeds for use in further DNA or protein extraction analysis.

BACKGROUND OF THE INVENTION

It is conventional practice in plant breeding or plant advancement experiments to grow plants from seeds of known parentage. The seeds are planted in experimental plots, growth chambers, greenhouses, or other growing conditions in which they are either cross pollinated with other plants of known parentage or self pollinated. The resulting seeds are the offspring of the two parent plants or the self pollinated plant, and are harvested, processed and planted to continue the plant breeding cycle. Specific laboratory or field-based tests may be performed on the plants, plant tissues, seed or seed tissues, in order to aid in the breeding or advancement selection process.

Generations of plants based on known crosses or self pollinations are planted and then tested, such as through trait purity tests, to see if these lines or varieties are moving toward characteristics that are desirable in the marketplace. Examples of desirable traits include, but are not limited to, increased yield, increased homozygosity, improved or newly conferred resistance and/or tolerance to specific herbicides and/or pests and pathogens, increased oil content, altered starch content, nutraceutical composition, drought tolerance, and specific morphological based trait enhancements.

Often, seeds having desirable characteristics are produced commercially for sale in the marketplace. In such instances, quality control tests, such as genetic purity tests, may be conducted to determine that the seeds indeed comprise the advertised genetic composition. In many instances, a certain number of seeds may be sampled from each bag of seeds produced. For example, it is not uncommon to test approximately one hundred seeds from each production bag in order to verify the genetic composition of the seeds from the bag. For some seed types, such as those in large production, this can translate to over one million individual seeds to be sampled.

In order to test the genetic composition of the seeds, samples of the individual seeds themselves, or of the plants that develop from the seeds, are gathered. For example, in one method, a hole is drilled in a small location on the seed and the debris from the seed is removed. The debris is then transferred to a test tube or other container and analyzed. Another method is described in V. Sangtong, E. C. Mottel, M. J. Long, M. Lee, and M. P. Scott, *Serial Extraction of Endosperm Drillings (SEED)—A Method for Detecting Transgenes and Proteins in Single Viable Maize Kernels*, Plant Molecular Biology Reporter 19: 151-158, June 2001, in which a hand-held rotary grinder is used to grind off so-called "drillings" from each kernel.

Automated seed grinding techniques also exist to generate seed samples. For example, in one method a blade grinder (or cutting mill) may be used to grind one or more seeds into a group of seed particles. In general, a typical blade grinder includes a chamber into which the one or more seeds may be placed, and one or more blades that are configured to rotate within the chamber such that they act upon the seed(s) so as to reduce the seed(s) into a group of seed particles. In another method, a shaker grinder (or ball mill) may be used to crush one or more seeds into a group of seed particles. In general, a typical shaker grinder includes a chamber into which the one or more seeds may be placed, and one or more "balls" that are placed into the chamber along with the seed(s). The chamber is then vibrated in such a manner that the grinding balls act upon the seed(s) to reduce the seed(s) into the group of seed particles.

For each of these methods, the seed samples are transferred by hand to a testing apparatus where the tissue samples from the seed(s) are analyzed for DNA or protein composition. Many procedures exist whereby various proteins or cell DNA may be extracted from the samples. For example, a typical method may include placing a seed sample into an extraction well and subjecting the seed sample cells to a cell lysis solution such that the cell walls are broken down to release the DNA and proteins into the resulting solution. A buffer may then be added that is formulated to separate the DNA from the proteins. At this point either the DNA or the protein may be extracted for further testing.

The above methods of obtaining seed samples from the seed chambers and transferring the samples to the testing apparatuses are extremely time consuming and involve numerous manual processes. In addition, it is difficult to obtain seed samples having repeatable sample sizes. As a result, there is a need for an improved system and method for obtaining tissue samples from one or more seeds. In various embodiments, the system and method should provide an efficient manner of gathering seed samples for further processing, such as DNA and protein purification and extraction, and it should also provide normalized seed sample sizes.

BRIEF SUMMARY OF VARIOUS EMBODIMENTS

The present invention addresses the above needs and achieves other advantages by providing a system and method of obtaining a sample from one or more seeds. In general, the method comprises placing at least one seed into a seed sampling chamber, breaking the seed into a plurality of seed particles inside the seed sampling chamber, placing a sampling element into the seed sampling chamber, and collecting at least a portion of the plurality of seed particles with the sampling element, wherein the collecting occurs by attracting at least a portion of the seed particles to a surface of the sampling element. In some embodiments, attracting at least a portion of the seed particles to a surface of the sampling element may occur through magnetic attraction. In some embodiments, attracting at least a portion of the seed particles to a surface of the sampling element may occur through static attraction. In some embodiments, attracting at least a portion of the seed particles to a surface of the sampling element may occur through mechanical attraction. In some embodiments, the mechanical attraction may be created by a surface finish of the sampling element. In some embodiments, the mechanical attraction may be created by a surface treatment of the sampling element. In some embodiments, the surface treatment may include applying a wax material to the surface of the sampling element.

In some embodiments, collecting at least a portion of the plurality of seed particles may comprise forcing at least a portion of the seed particles into a feature of the sampling element. In some embodiments, collecting at least a portion of the plurality of seed particles may comprise forcing at least a portion of the seed particles into a cavity of the sampling element. In some embodiments, collecting at least a portion of the plurality of seed particles may comprise forcing at least a portion of the seed particles into one or more passages extending through the sampling element. In some embodiments, collecting at least a portion of the plurality of seed particles may comprise forcing at least a portion of the seed particles into one or more grooves of the sampling element. In some embodiments, placing a sampling element into the seed sampling chamber may comprise placing into the seed sampling chamber a sampling element having a shape selected from the group consisting of ball-shaped, oval-shaped, and anvil-shaped. In some embodiments, the step of placing the sampling element into the seed sampling chamber may occur before the step of breaking the seed into a plurality of seed particles. In some embodiments, the step of placing the sampling element into the seed sampling chamber may occur after the step of breaking the seed into a plurality of seed particles. In some embodiments, the step of breaking the seed into a plurality of seed particles may comprise shaking the seed sampling chamber such that the sampling element breaks the seed into the plurality of seed particles.

Some embodiments may further comprise removing the sampling element containing the collected portion of seed particles from the seed sampling chamber, releasing the sampling element into an extraction well, and extracting at least one of DNA or proteins from the collected portion of seed particles. In some embodiments, the sampling element may be removed from the seed sampling chamber using a sampling element transfer device. In some embodiments, the sampling element may include magnetically responsive content and the sampling element transfer device may include a removal rod and a deflector plate, and the sampling element may be removed from the seed sampling chamber using a magnet located proximate an end of the removal rod, and the sampling element may be released into the extraction well by deflecting the sampling element from the removal rod using the deflector plate. In some embodiments, the sampling element may include magnetically responsive content and the sampling element transfer device may include an electromagnet operating under an electric current, and the sampling element may be removed from the seed sampling chamber using the electromagnet, and the sampling element may be released into the extraction well by removing the electric current from the electromagnet.

Another embodiment of the present invention provides a system for obtaining a sample from a seed. In general, the system comprises a seed sampling device that includes a seed sampling chamber configured to receive at least one seed, and a sampling element configured to be placed into the seed sampling chamber, wherein the seed sampling device is configured to break the seed into a plurality of seed particles inside the seed sampling chamber, and wherein the sampling element is further configured to collect at least a portion of the plurality of seed particles by attracting at least a portion of the seed particles to a surface of the sampling element. In some embodiments, the sampling element may be configured to collect at least a portion of the plurality of seed particles by attracting seed particles to a surface of the sampling element through magnetic attraction. In some embodiments, the sampling element may be configured to collect at least a portion of the plurality of seed particles by attracting seed particles to a surface of the sampling element through static attraction. In some embodiments, the sampling element may be configured to collect at least a portion of the plurality of seed particles by attracting seed particles to a surface of the sampling element through mechanical attraction. In some embodiments, the sampling element may include a surface finish configured to create the mechanical attraction. In some embodiments, the sampling element may include a surface treatment configured to create the mechanical attraction. In some embodiments, the surface treatment may be a wax material.

In some embodiments, the sampling element may be configured to collect at least a portion of the plurality of seed particles by receiving at least a portion of the seed particles into a feature of the sampling element. In some embodiments, the sampling element may be configured to collect at least a portion of the plurality of seed particles by receiving at least a portion of the seed particles into a cavity of the sampling element. In some embodiments, the sampling element may be configured to receive at least a portion of the seed particles into one or more passages extending through the sampling element.

In some embodiments, the sampling element may be configured to collect at least a portion of the plurality of seed particles by receiving at least a portion of the seed particles into one or more grooves of the sampling element. In some embodiments, the sampling element may have a shape selected from the group consisting of ball-shaped, oval-shaped, and anvil-shaped. In some embodiments, the seed sampling device may be configured to shake the seed sampling chamber and the sampling element may be configured to break the seed into the plurality of seed particles.

Some embodiments further comprise an extraction well configured for receiving the sampling element and for receiving a solution configured to extract at least one of DNA or proteins from the collected portion of seed particles. Some embodiments further comprise a sampling element transfer device configured to remove the sampling element from the seed sampling chamber. In some embodiments, the sampling element may include magnetically responsive content and the sampling element transfer device may include a removal rod and a deflector plate, and the removal rod may be configured to remove the sampling element from the seed sampling chamber using a magnet located proximate an end of the removal rod, and the deflector plate may be configured to release the sampling element into the extraction well by deflecting the sampling element from the removal rod. In some embodiments, the sampling element may include magnetically responsive content and the sampling element transfer device may include an electromagnet, and the electromagnet may be configured to remove the sampling element from the seed sampling chamber by operating under an electric current, and the electromagnet may be configured to release the sampling element into the extraction well by removing the electric current from the electromagnet.

BRIEF DESCRIPTION OF THE DRAWINGS

Figure 1:
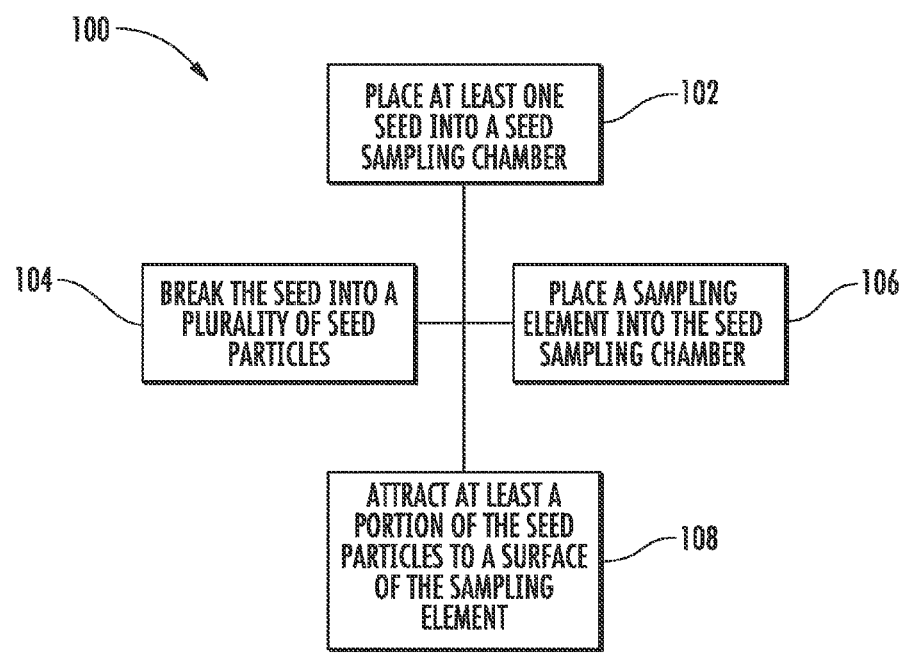
Figure 2:
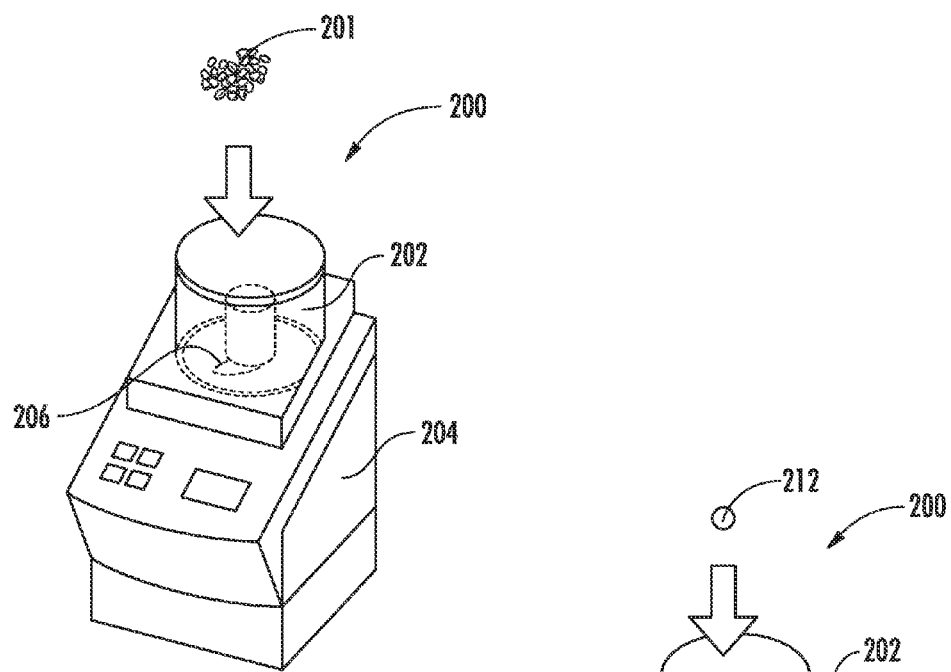
Figure 2A:
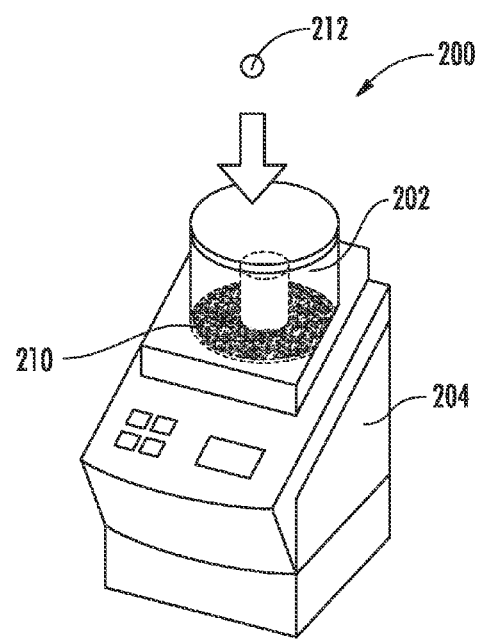
Figure 3:
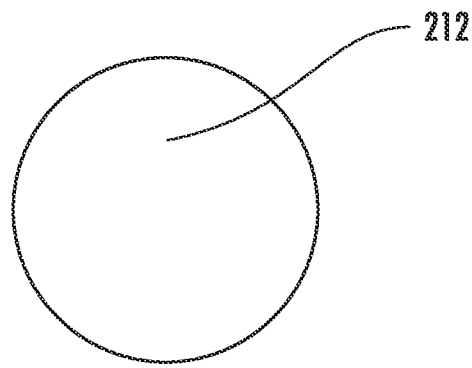
Figure 3A:
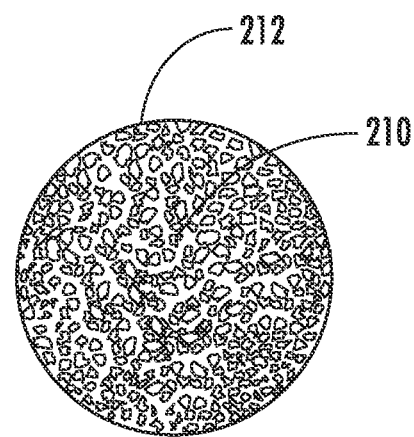
Figure 4:
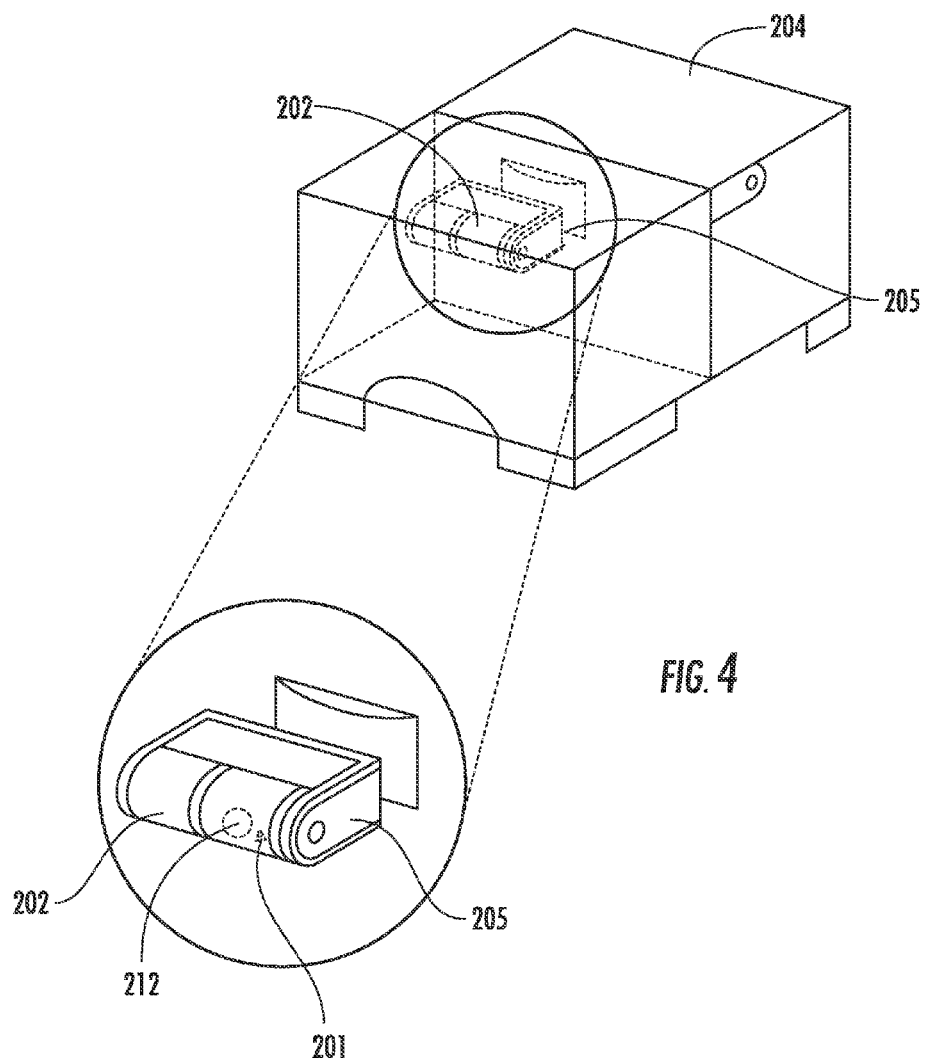
Figure 5:
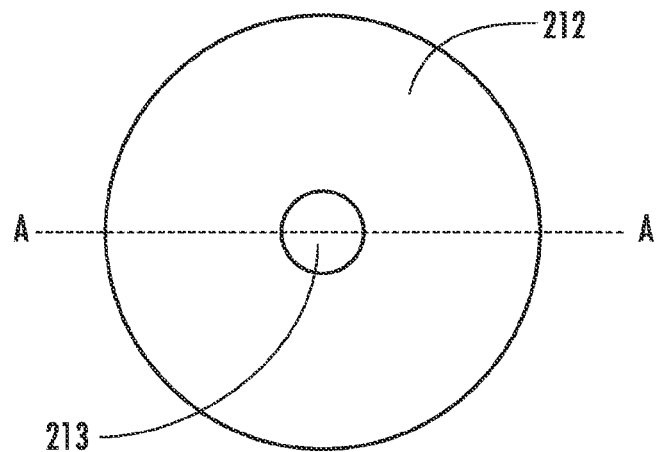
Figure 5A:
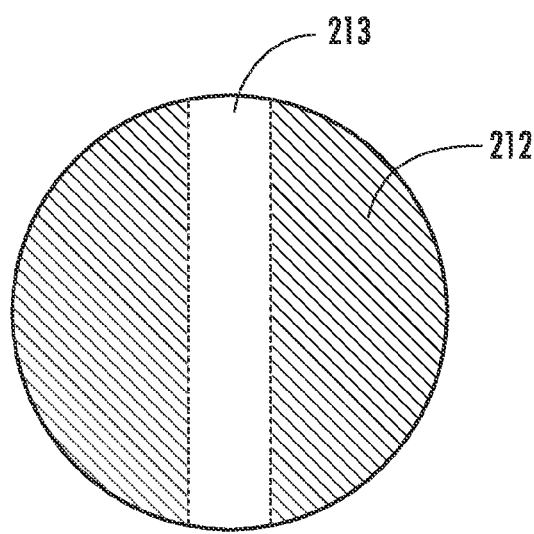
Figure 6:
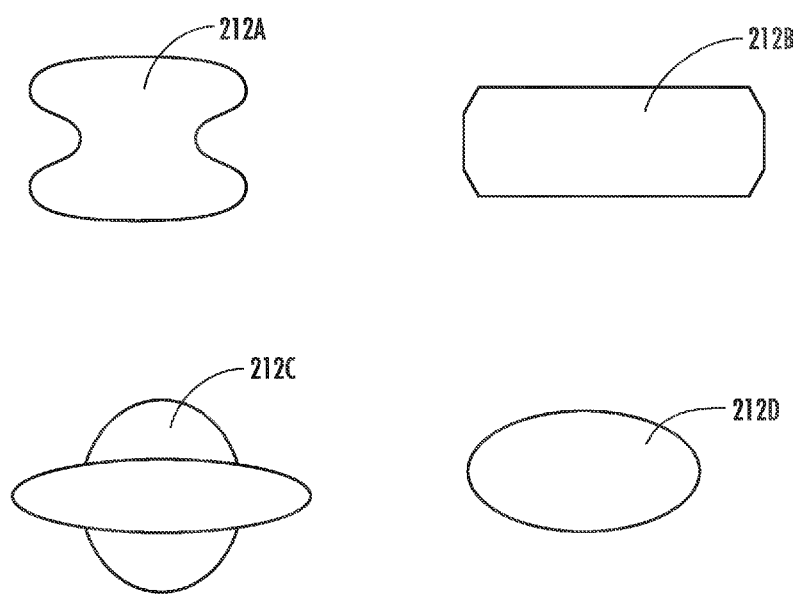
Figure 7:
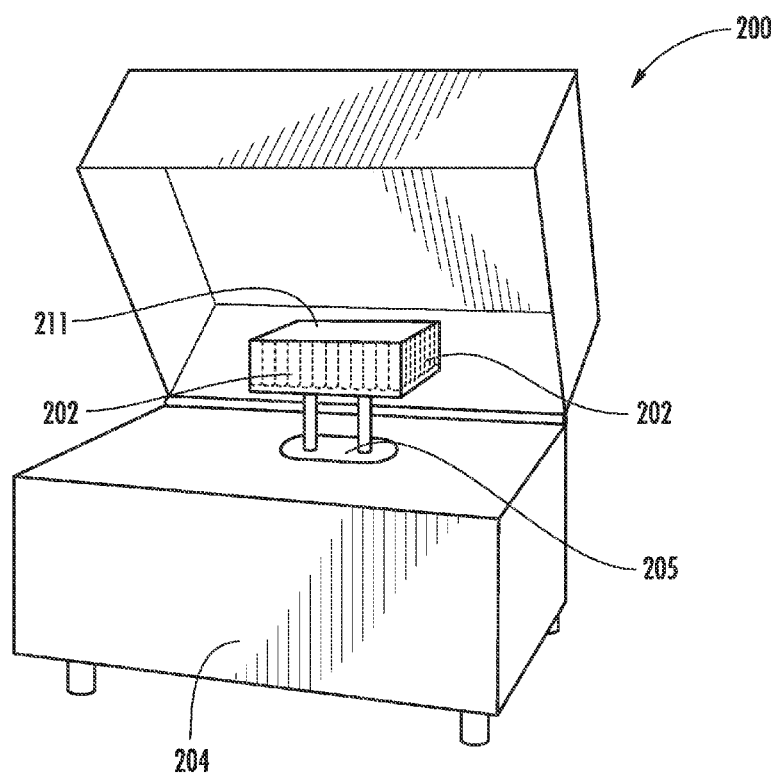
Figure 8:
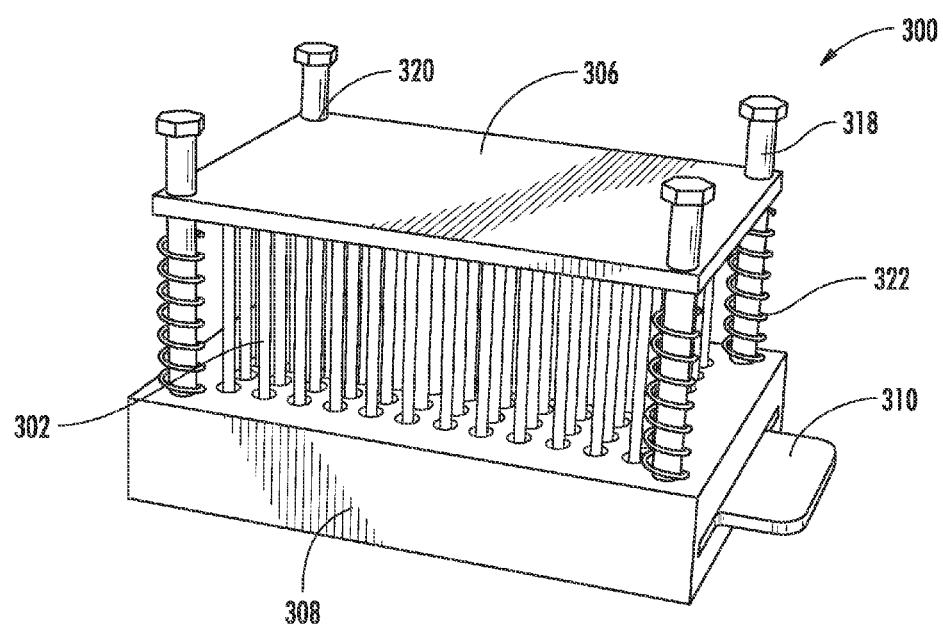
Figure 9:
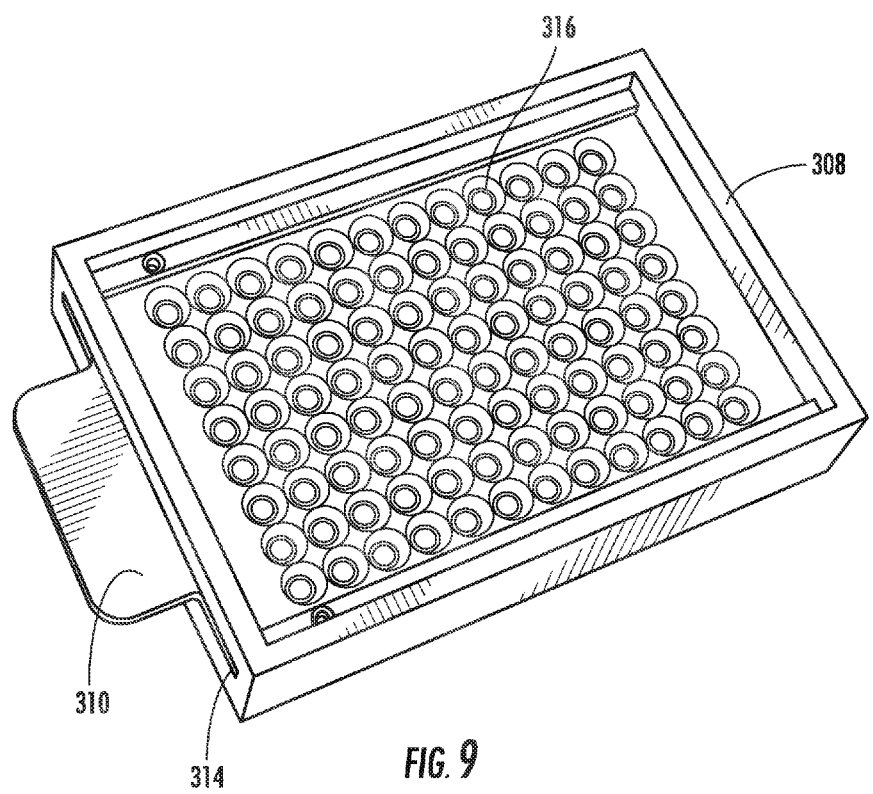
Figure 10:
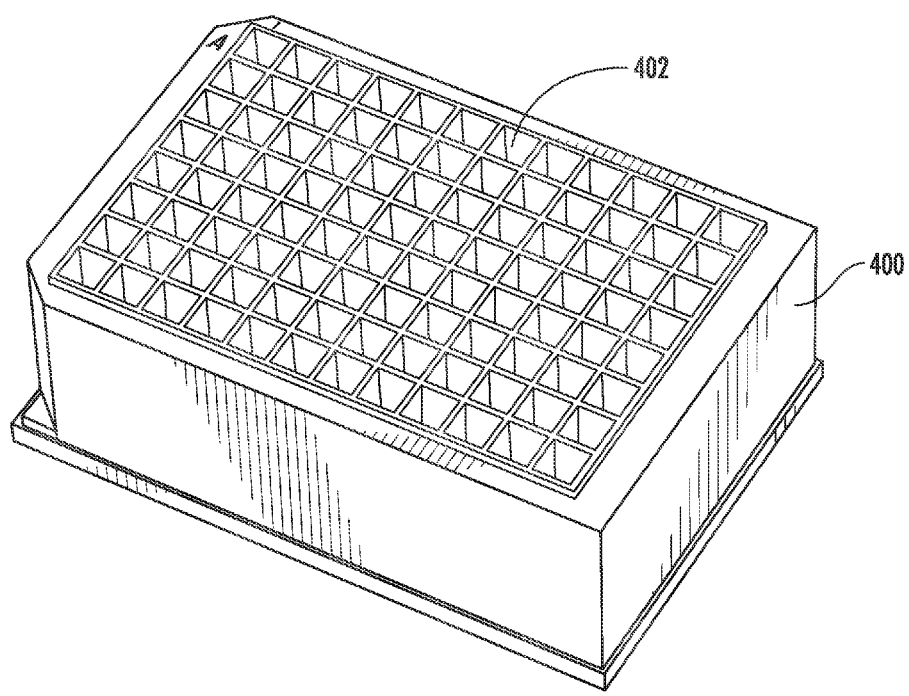

Having thus described the invention in general terms, reference will now be made to the accompanying drawings, which are not necessarily drawn to scale, and wherein:

FIG. 1 shows a flow chart of a method, according to one embodiment of the present invention, including steps for placing at least one seed into a seed sampling chamber, placing a sampling element into the seed sampling chamber, breaking the seed into a plurality of seed particles, and attracting at least a portion of the seed particles to a surface of the sampling element;

FIG. 2 shows a perspective view of seeds being placing into a seed sampling chamber of a seed sampling device in accordance with an exemplary embodiment of the present invention;

FIG. 2A shows a perspective view of a sampling element being placed into the seed sampling chamber of the seed sampling device of FIG. 2 in accordance with an exemplary embodiment of the present invention;

FIG. 3 shows a perspective view of an outer surface of a sampling element in accordance with an exemplary embodiment of the present invention;

FIG. 3A shows a perspective view of an outer surface of a sampling element that has attracted a plurality of seed particles in accordance with an exemplary embodiment of the present invention;

FIG. 4 shows a perspective view of a seed sampling device and a detailed perspective view of the seed sampling chamber of the seed sampling device configured to execute a method of obtaining a seed sample in accordance with another exemplary embodiment of the present invention;

FIG. 5 shows a top view of a sampling element having a collection feature in accordance with another exemplary embodiment of the present invention;

FIG. 5A shows a cross-section view of the sampling element of FIG. 5;

FIG. 6 shows a perspective view of sampling elements in accordance with other embodiments of the present invention;

FIG. 7 shows a perspective view of a seed sampling device configured to execute a method of obtaining a seed sample in accordance with another exemplary embodiment of the present invention;

FIG. 8 shows a perspective view of a sampling element transfer device in accordance with an exemplary embodiment of the present invention;

FIG. 8A shows an exploded perspective view of the sampling element transfer device of FIG. 8;

FIG. 9 shows a perspective view from a different angle of a bottom plate and a deflector plate of a sampling element transfer device in accordance with an exemplary embodiment of the present invention; and FIG. 10 shows a seed particle collector having a plurality of extraction wells in accordance with an exemplary embodiment of the present invention.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

As will be described below, the present invention is generally directed to a system and method for obtaining a sample from a seed or seeds. FIG. 1 shows a general flowchart illustrating a method 100 for obtaining a sample from a seed in accordance with one exemplary embodiment of the present invention. In step 102, at least one seed is placed into a sampling chamber. It should be noted that in some embodiments a single seed may be placed in the sampling chamber, while in other embodiments two or more seeds may be placed in the sampling chamber. In step 104, the seed is broken into a plurality of seed particles inside the seed sampling chamber. As will be discussed in more detail below, some embodiments may use a single seed sampling chamber, while other embodiments may use two or more seed sampling chambers. Additionally, in some embodiments this step may comprise, for example, breaking the seed into a plurality of seed particles using blades of a blade grinder-type seed sampling device, or breaking the seed or seeds into a plurality of seed particles using a shaker-type seed sampling device. In some embodiments utilizing a shaker-type seed sampling device, the seed sampling element itself breaks the seed into the plurality of seed particles.

In step 106, a sampling element is placed into the seed sampling chamber. In various embodiments, this step may occur prior to, after, or at the same time that the seeds are broken into a plurality of seed particles. In step 108, at least a portion of the plurality of seed particles is collected with the sampling element. In various embodiments, this may occur by attracting at least a portion of the seed particles to a surface of the sampling element through magnetic attraction, static attraction, mechanical attraction, or any combinations thereof. In some embodiments, this may occur by forcing at least a portion of the seed particles into a feature of the sampling element. In some embodiments, the method may further include using a sampling element transfer device to transfer the sampling element to an extraction well, which may be used to extract DNA or proteins from the collected portion of seed particles.

FIG. 2 shows a perspective view of a seed sampling device 200 configured to carry out a method of obtaining a sample from a seed in accordance with an exemplary embodiment of the present invention. In general, the seed sampling device 200 of the depicted embodiment comprises a seed sampling chamber 202 and a main body 204. In the depicted embodiment, the seed sampling device 200 is configured as a blade grinder (or cutting mill), which includes one or more blades 206 that rotate within the seed sampling chamber 202. In the depicted embodiment, the main body 204 of the seed sampling device 200 houses various devices and/or mechanisms that generate and control the action of the blade(s) 206. The seed sampling device 200 of the depicted embodiment is configured to rotate the blade(s) 206 so as to grind one or more seeds 201 into a group of seed particles 210, from which a sample comprising at least a portion of the seed particles may be taken. Although a variety of devices may be used, a suitable seed sampling device for use with similar embodiments may be a Grindomix GM200 available from Retsch GmbH of Haan, Germany. In other embodiments, various other devices may be used to break the seeds into a plurality of seed particles, including, but not limited to jaw crushers, rotor mills, mortar grinders, disc mills, and ball mills.

FIG. 2A shows a perspective view of the seed sampling device 200 of FIG. 1 showing the group of seed particles 210 that was generated after grinding the plurality of seeds 201 shown in FIG. 2. Also shown in FIG. 2A is a sampling element 212 that, in the depicted embodiment, is placed into the seed sampling chamber 202 after the seeds 201 have been ground into the group of seed particles 210. As will be discussed below, in various embodiments the sampling element may be placed into the sampling chamber before, after, or at the same time the seed(s) are broken into a group of seed particles. In some embodiments, the sampling element may facilitate breaking the seed(s) into the group of seed particles. In the depicted embodiment, the sampling element 212 is a 5/32 inch diameter steel ball bearing having a substantially spherical shape, however in other embodiments the sampling element may have a variety of shapes and sizes (for a non-limiting group of examples, see FIGS. 5-6), and may be made of a variety of materials, including, but not limited to, various metal and plastic materials, and combinations thereof. Sampling elements of various embodiments may also include magnetically responsive content, including, but not limited to, ferrous materials and materials that include ferrous content. It should be noted that in the depicted embodiment, the seed sampling device 200 grinds a plurality of seeds 201 to generate the group of seed particles 210, however, in other embodiments, the seed sampling device 200 may be used to grind any number of seeds, including as few as a single seed, to generate a group of seed particles. It should also be noted that although some of the figures referred to herein depict seeds in the form of corn seeds, the systems and methods of the present invention are applicable to any other type of seed and to any other element comprising a tissue structure from which samples may be taken, including, but not limited to, vegetable seeds, flower seeds, rapeseeds, rice seeds, wheat seeds, canola seeds, soybean seeds, sunflower seeds, sorghum seeds, etc.

In various embodiments, a portion of the seed particles 210 are collected with the sampling element 212 by attracting at least a portion of the seed particles 210 to a surface of the sampling element 212. In the depicted embodiment, the sampling element 212 includes a surface treatment comprising applying a wax material to the surface of the sampling element 212 such that at least a portion of the seed particles are attracted to the sampling element 212 through mechanical attraction. However, in various other embodiments, at least a portion of the seed particles 210 may be collected by the sampling element 212 through any means of attraction of the seed particles, including, but not limited to, magnetic attraction, static attraction, mechanical attraction, or any combinations thereof. In some embodiments attraction of the seed particles may be effected without any surface treatment or finish of sampling element, while in other embodiments, various surface treatments, finishes, and/or features of the sampling element may facilitate attraction of seed particles. For example, the sampling element of some embodiments may include a rough surface finish, a tacky surface treatment, or a static or magnetic charge that facilitates attraction of at least a portion of the seed particles.

FIG. 3 shows a close-up view of the sampling element 212 of one embodiment prior to being placed into a sampling chamber. FIG. 3A shows the sampling element 212 of one embodiment after attracting at least a portion of the seed particles 210 to the surface of the sampling element 212. In various embodiments, collecting at least a portion of the plurality of seed particles according to the methods described herein may also provide for collecting and transferring normalized seed sample sizes. For example, in the depicted embodiment, the seed sample size may be normalized due to the finite nature of the surface area of the sampling element. Thus, predictable seed sample sizes may be gathered by using sampling elements having collecting surfaces with known surface areas. In such a manner, for example, by using the same sampling element or by using various sampling elements having substantially similar designs or by using various sampling elements having substantially similar collecting surface area sizes, various seed samples may be collected that have substantially similar seed sample sizes.

In some embodiments, after collecting at least a portion of the seed particles 210, the method of obtaining a sample from a seed in accordance with the present invention may further comprise removing the sampling element 212 from the sampling chamber and releasing the sampling element into an extraction well. Once in the extraction well, the procedure may comprise extracting DNA and/or proteins from the collected portion of seed particles. In various embodiments the DNA and/or proteins may be extracted through various procedures. For example, in one exemplary procedure a cell lysis solution may be added to the seed particles that breaks down seed particles and separates the DNA and proteins. Next, through centrifuge, decanting, or otherwise, the DNA may be separated from the proteins. As will be discussed in more detail below, in some embodiments the sampling element 212 may be removed from the sampling chamber and transferred to the extraction well using a sampling element transfer device.

As noted above, in some embodiments the sampling element that collects at least a portion of the plurality of seed particles may be placed into the seed sampling chamber after the seed or seeds have been broken into a plurality of seed particles, and in other embodiments the sampling element that collects at least a portion of the plurality of seed particles may be placed into the seed sampling chamber prior to the seed or seeds being broken into a plurality of seed particles. In still other embodiments, the sampling element may break the seed or seeds into the plurality of seed particles and collect at least a portion of the plurality of seed particles. An example of such an embodiment is depicted in FIG. 4.

FIG. 4 shows a perspective view of a seed sampling device 200 configured to execute a method of obtaining a seed sample in accordance with another exemplary embodiment of the present invention. In general, the seed sampling device 200 of the depicted embodiment comprises a seed sampling chamber 202 and a main body 204. In the depicted embodiment, the seed sampling device is configured as a shaker-type seed sampling device, which includes a shaking device 205 configured to shake the seed sampling chamber 202. The main body 204 of the seed sampling device 200 of the depicted embodiment houses various devices and/or mechanisms that generate and control the action of the shaking device 205.

In various embodiments, a shaker-type seed sampling device is configured to shake a seed sampling chamber containing one or more seeds. In some embodiments, the seed or seeds may be alone in the seed sampling chamber, however in other embodiments the seed sampling chamber may include an additional article configured to break the seed or seeds into a plurality of seed particles. In the depicted embodiment, the seed sampling chamber 202 includes a single seed 201 and a single sampling element 212. Although the configuration of a sampling element may be different in various embodiments, in the depicted embodiment the sampling element 212 comprises a substantially spherical steel ball bearing. In the depicted embodiment, the seed sampling device 200 is configured to shake the seed sampling chamber 202. The seed sampling element 212 of the depicted embodiment is configured to both break the seed 201 into the plurality of seed particles and to collect at least a portion of the resulting plurality of seed particles. It should be noted that although the depicted embodiment shows a single seed and a single sampling element, other embodiments may have two or more seeds and/or two or more sampling elements. Such embodiments may also include sampling elements that have different configurations. Other embodiments may have one or more sampling elements in addition to one or more other articles configured to break the seed or seeds into a plurality of seed particles.

In various embodiments, a portion of the seed particles are collected with the sampling element 212 by attracting at least a portion of the seed particles to a surface of the sampling element 212. In the depicted embodiment, the sampling element 212 includes a surface finish such that at least a portion of the seed particles are mechanically collected on the sampling element 212. However, in various embodiments, at least a portion of the seed particles may be collected by the sampling element 212 through any means of attraction of the seed particles, including, but not limited to, magnetic attraction, static attraction, mechanical attraction, or any combinations thereof. In some embodiments attraction of the seed particles may be effected without any surface finish or treatment of sampling element, while in other embodiments, various surface treatments, finishes, and/or features of the sampling element may facilitate attraction of seed particles.

Other embodiments of the sampling element may include one or more collection features that facilitate attraction of at least a portion of the seed particles. Such collection features may include, but need not be limited to, one or more cavities, one or more grooves, and/or one or more passageways configured to collect at least a portion of the seed particles. FIGS. 5 and 5A show a top view and a cross-section view, respectively, of a sampling element 212 having a collection feature 213 in accordance with another exemplary embodiment of the present invention. In the depicted embodiment, the sampling element 212 is a substantially spherical steel ball bearing having a collection feature 213 that comprises a passageway that extends through the sampling element 212. In those embodiments where the sampling element comprises a collection feature, at least a portion of the plurality of seed particles may be forced into the collection feature. Thus, in the depicted embodiment, at least a portion of the plurality of seed particles may be forced into the passageway. Such embodiments depict another way in which normalized seed sample sizes may be collected by the sampling element 212.

Although the sampling elements described and depicted thus far have been substantially spherical in shape and have been made of a steel material, sampling elements of various other embodiments may have a variety of different shapes and may be made of variety of materials. For example, FIG. 6 shows a front view of various sampling elements having other exemplary shapes in accordance with other embodiments of the present invention. Sampling element 212A is substantially anvil-shaped, sampling element 212B is substantially pin-shaped, sampling element 212C is substantially ballcone shaped, and sampling element 212D is substantially oval-shaped. It should be noted that FIG. 6 represents a small sample of possible sampling element shapes, thus, the shape of a sampling element should not be limited to those presented in the figures. Likewise, although the sampling elements described thus far have been constructed of a steel material, sampling elements of various other embodiments may be constructed of other materials or a combination of other materials. For example, sampling elements other embodiments may be constructed of other metal materials, plastic materials, composite materials, organic materials, and/or combinations thereof.

FIG. 7 shows a perspective view of a seed sampling device 200 configured to execute a method of obtaining a seed sample in accordance with another exemplary embodiment of the present invention. In general, the seed sampling device 200 of the depicted embodiment comprises a main body 204 and a container 211 that includes a plurality of seed sampling chambers 202. The seed sampling device 200 of the depicted embodiment is configured as a ball mill or shaker-type seed sampling device, which includes a shaking device 205 configured to shake the plurality of seed sampling chambers 202. Although a variety of devices may be used, a suitable seed sampling device for use with similar embodiments may be a Geno/Grinder 2000 available from SPEX CertiPrep, Inc. of Metuchen, N.J. The main body 204 of the seed sampling device 200 of the depicted embodiment houses various devices and/or mechanisms that generate and control the action of the shaking device 205. Although a variety of configurations are possible, in the depicted embodiment the container 211 houses 96 seed sampling chambers arranged in an 8×12 array.

Although in various embodiments any number of seeds or sampling elements may be used, in the depicted embodiment, each of the plurality of seed sampling chambers 202 includes one seed (not visible in this figure) and a sampling element (also not visible in this figure). In the depicted embodiment, each sampling element breaks a respective seed into respective pluralities of seed particles and collects at least a portion of the respective seed particles. The sampling element of the depicted embodiment also comprises magnetically responsive content. In various embodiments, the plurality of sampling chambers 202 may include the same types of seeds, different types of seeds, or combinations thereof. Additionally, in other embodiments other components may be used to break the seeds into the respective pluralities of seed particles such that the sampling elements may be introduced into the sampling chambers after the seeds have been broken.

FIGS. 8 and 8A show a sampling element transfer device 300 in accordance with an exemplary embodiment of the present invention. The sampling element transfer device 300 of the depicted embodiment is configured to be used to transfer respective sampling elements 212 from seed sampling chambers 202 into a plurality of respective extraction wells so as to extract DNA or proteins from the collected portions of seed particles. The sampling element transfer device 300 of the depicted embodiment comprises a plurality of removal rods 302, each with a respective magnet component 304 located proximate a lower end thereof. Although a variety of configurations are possible, in the depicted embodiment there are ninety-six (96) removal rods fixedly arranged within a top-plate 306 so that the removal rods form an eight by twelve (8×12) array. The sampling element transfer device 300 also includes a bottom plate 308 and a deflector plate 310. In the depicted embodiment, the bottom plate 308 includes a plurality of apertures 312 also arranged in an eight by twelve (8×12) array and configured to receive the plurality of removal rods 302. The deflector plate 310 is configured to be received into a slot 314 of the bottom plate 308 and includes a plurality of apertures 316 arranged in an 8×12 array and configured to align with the plurality of apertures 312 of the bottom plate 308. The plurality of apertures 316 of the deflector plate 310 is also configured to receive the plurality of removal rods 302. FIG. 9 shows the underside of the bottom plate 308 and the deflector plate 310. Although many other configurations are possible, the bottom side of the deflector plate apertures 316 are countersunk so that various sizes and shapes of sampling elements may be accommodated by the apertures 316 but not pass through the apertures 316.

Referring back to FIGS. 8 and 8A, in an assembled state, the top plate 306 is joined to the bottom plate 308 via four attachment rods 318 such that the plurality of removal rods 302 extend through the plurality of apertures 312 of the bottom plate 308 and the plurality of apertures 316 of the deflector plate 310 as shown in FIG. 8. The top plate 306, which also includes four guide holes 320, is configured to guide the plurality of removal rods 302 through the apertures 312 of the bottom plate 308 and the apertures 316 of the deflector plate 310 by traveling along the attachment rods 318. Each of the attachment rods 318 receives around it a spring 322 such that the springs 322 resist the movement of the top plate 306 toward the bottom plate 308 and thus the plurality of removal rods 302 through the plurality of apertures 312, 316.

In various embodiments, a sampling element transfer device may be used after a seed or seeds have been broken into a plurality of seed particles. The plurality of removal rods 302 of the sampling element transfer device 300 of the depicted embodiment is arranged in an array to be used with a plurality of seed sampling chambers having a similar array configuration (such as, for example, the plurality of seed sampling chambers 202 of FIG. 7). In such a manner, each removal rod 302 aligns with a respective seed sampling chamber 202 such that the sampling element transfer device 300 may be placed over the plurality of seed sampling chambers and the top plate 306 of the sampling element transfer device 300 may be compressed toward the bottom plate 308 so that the removal rods 302 extend through the apertures 316 of the deflector plate 310 and into the plurality of seed sampling chambers. As such, because the sampling elements of the depicted embodiment include magnetically responsive content, the magnetic components 304 located on each of the removal rods 302 may pick up the sampling elements contained in each of the seed sampling chambers. The sampling element transfer device 300 may then be placed above a plurality of extraction wells arranged in a similar configuration, and the sampling elements may be released into respective extraction wells.

Although the sampling element transfer device of the depicted embodiment is configured to transfer a plurality of sampling elements out of a plurality of seed sampling chambers having a particular arrangement, in other embodiments sampling element transfer devices may be configured to transfer sampling elements out of seed sampling chambers having other configurations. Additionally, a sampling element transfer device may be configured to transfer a single sampling element. Also, although the depicted embodiment uses permanent magnets, in other embodiments a sampling element transfer device may include an electromagnet.

FIG. 10 shows a seed particle collector 400 that includes a plurality of extraction wells 402. Although a variety of configurations are possible, the seed particle collector 400 of the depicted embodiment includes ninety-six (96) extraction wells 402 arranged in an eight by twelve (8×12) array. In such a manner, the sampling elements picked up by the plurality of removal rods 302 of the sampling element transfer device 300 may be aligned with the plurality of extraction wells 402, and the top plate 306, which had been compressed toward the bottom plate 308, may then be released such that the plurality of removal rods 302 retract through the apertures 316. In such a manner, the plurality of sampling elements are deflected by deflector plate apertures 316 and into respective ones of the plurality of extraction wells 402. Further processing may then be undertaken on the seed particles collected by each of the plurality of sampling elements. Such further processing may include separating DNA and/or proteins from the seed particles as described above. This may be accomplished in one embodiment, for example, by adding a cell lysis solution to the extraction wells that breaks down seed particles and separates the DNA and proteins, and then, through centrifuge, decanting, or otherwise, separating the DNA from the proteins.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for obtaining a sample from a seed, said system comprising:
   a seed sampling device that includes a seed sampling chamber configured to receive at least one seed; and
   a sampling element configured to be placed into the seed sampling chamber,
   wherein the seed sampling device is configured to break the seed into a plurality of seed particles inside the seed sampling chamber, and wherein the sampling element is further configured to collect at least a portion of the plurality of seed particles by attracting at least a portion of the seed particles to a surface of the sampling element.

2. The system of claim 1, wherein the sampling element is configured to collect at least a portion of the plurality of seed particles by attracting seed particles to a surface of the sampling element through magnetic attraction.

3. The system of claim 1, wherein the sampling element is configured to collect at least a portion of the plurality of seed particles by attracting seed particles to a surface of the sampling element through static attraction.

4. The system of claim 1, wherein the sampling element is configured to collect at least a portion of the plurality of seed particles by attracting seed particles to a surface of the sampling element through mechanical attraction.

5. The system of claim 4, wherein the sampling element includes a surface finish configured to create the mechanical attraction.

6. The system of claim 4, wherein the sampling element includes a surface treatment configured to create the mechanical attraction.

7. The system of claim 6, wherein the surface treatment is a wax material.

8. The system of claim 1, wherein the sampling element is configured to collect at least a portion of the plurality of seed particles by receiving at least a portion of the seed particles into a feature of the sampling element.

9. The system of claim 8, wherein the sampling element is configured to collect at least a portion of the plurality of seed particles by receiving at least a portion of the seed particles into a cavity of the sampling element.

10. The system of claim 8, wherein the sampling element is configured to receive at least a portion of the seed particles into one or more passages extending through the sampling element.

11. The system of claim 8, wherein the sampling element is configured to collect at least a portion of the plurality of seed particles by receiving at least a portion of the seed particles into one or more grooves of the sampling element.

12. The system of claim 1, wherein the sampling element has a shape selected from the group consisting of:
   ball-shaped;
   oval-shaped; and
   anvil-shaped.

13. The system of claim 1, wherein the seed sampling device is configured to shake the seed sampling chamber and the sampling element is configured to break the seed into the plurality of seed particles.

14. The system of claim 1, further comprising an extraction well configured for receiving the sampling element and for receiving a solution configured to extract at least one of DNA or proteins from the collected portion of seed particles.

15. The system of claim 14, further comprising a sampling element transfer device configured to remove the sampling element from the seed sampling chamber.

16. The system of claim 15, wherein the sampling element includes magnetically responsive content and the sampling element transfer device includes a removal rod and a deflector plate, and wherein the removal rod is configured to remove the sampling element from the seed sampling chamber using a magnet located proximate an end of the removal rod, and the deflector plate is configured to release the sampling element into the extraction well by deflecting the sampling element from the removal rod.

17. The system of claim 15, wherein the sampling element includes magnetically responsive content and the sampling element transfer device includes an electromagnet, and wherein the electromagnet is configured to remove the sampling element from the seed sampling chamber by operating under an electric current, and wherein the electromagnet is configured to release the sampling element into the extraction well by removing the electric current from the electromagnet.

\* \* \* \* \*